US010775373B2

(12) United States Patent
Wang et al.

(10) Patent No.: US 10,775,373 B2
(45) Date of Patent: Sep. 15, 2020

(54) METHOD FOR ENHANCEMENT OF THE UNIFORM REACTION ON THE POROUS MATERIALS

(71) Applicant: National Taiwan University, Taipei (TW)

(72) Inventors: An-Bang Wang, Taipei (TW); Shih-Chung Chang, Taipei (TW); Chao-Yuan Liu, Taipei (TW); Yi-Wei Jiang, Taipei (TW); Yi-Kuang Yen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 502 days.

(21) Appl. No.: 15/602,136

(22) Filed: May 23, 2017

(65) Prior Publication Data

US 2018/0156789 A1 Jun. 7, 2018

(30) Foreign Application Priority Data

Dec. 1, 2016 (TW) ............................ 105139709 A

(51) Int. Cl.
*G01N 33/543* (2006.01)

(52) U.S. Cl.
CPC ..... *G01N 33/54393* (2013.01); *G01N 33/543* (2013.01)

(58) Field of Classification Search
USPC ............................................... 427/2.11, 2.13
See application file for complete search history.

(56) References Cited

U.S. PATENT DOCUMENTS

| | | | | |
|---|---|---|---|---|
| 9,492,836 | B2 * | 11/2016 | Wang | B05C 5/00 |
| 2003/0175827 | A1 * | 9/2003 | Stillman | G01N 33/552 435/7.9 |

OTHER PUBLICATIONS

Yen et al, "Western Blotting by Thin-Film Direct Coating", Analytical Chemistry, 2014, 86, 5164-5170. (Year: 2014).*
Chao-Yuan Liu et al., "Easy and Fast Western Blotting by Thin-Film Direct Coating with Suction", American Chemical Society, Jun. 2, 2016, pp. 6349-6356.
An-Bang Wang et al., "Miniaturization of Thin-Film Direct Coating Technology for New Biomedical Applications", Sep. 21, 2016, 18th International Coating Science and Technology Symposium(2016).

* cited by examiner

*Primary Examiner* — Christopher L Chin
(74) *Attorney, Agent, or Firm* — Bacon & Thomas, PLLC

(57) ABSTRACT

The present invention provides a method for enhancement of the uniform reaction on the porous materials. Comparing with the conventional Western blotting method, the present invention is successfully demonstrated capability on increasing the immune-detection signal intensity and only needs one order of magnitude less of the processing time by applying two orders of magnitude less dosage usage-amount compared to those operated in the conventional method.

1 Claim, 2 Drawing Sheets

METHOD FOR ENHANCEMENT OF THE UNIFORM REACTION ON THE POROUS MATERIALS

BACKGROUND OF THE INVENTION

1. Field of the Invention

The present invention relates to a method for the uniform reaction on the porous materials, particularly to a method for enhancement of the uniform reaction on the porous materials.

2. Description of the Prior Art

According to the estimation of Ministry of Economic Affairs, the annual market scale of the detection reagents in Taiwan is about NT$ 3,000 million. The annual market scale of the in vitro detection reagents is over NT$ 5,000 million in the world. If the relevant diagnostic detection reagents are included, the annual market scale has already been up to US$ 30,000 million. Wherein, the immune-detection reagents account for 25%, and the clinical chemistry detection reagents account for 16.5%. It reveals that the immune-detection reagents have already become the mainstream of the detection reagent market.

Wherein, in the market of the detection reagent, the need of application for the uniformly coated biochemical molecules on the test piece, membrane, chip, plastics, metal, filter paper, organic material, medical-grade product or the substance made by the other biochemical molecules etc. become more and more important. Especially, in the case of the biochemical molecules which are scarce or expensive with the high unit price, a key technology for quickly and uniformly coating the microscale biochemical molecules has become extremely important.

In the recent years, the biomedical detection carried out by the immunoreaction mechanism has already been widely applied in different fields, such as HIV immunodetection, Lyme disease detection, Hepatitis B virus detection, the tumor marker screening, the health examination, and the various regular blood and urine detections etc. However, when the protein or antigen is analyzed by the immunodetection, the detection process is commonly lengthy with the needs of high-price antibodies, combining with high-efficient catalysis of enzyme to reach high sensitive detection. Therefore, how to reduce the antibody consumption without sacrificing the signal intensity and also to save the reaction time has become the key issue to reach the fast precision immunodetection.

In the conventional Western blotting method, the membrane is put in a container containing the antibody, and the antibody is reacted with the target protein mainly via the diffusion mechanism. The mechanism of conventional Western blotting method is to combine the antibody exclusively, then the enzyme is used to display the color of the combined samples. The specific tissue or cell sample containing target protein is analyzed through the position of color and the density of color band. The target protein is then transferred onto a polyvinylidene fluoride (PVDF) membrane and immersed in an antibody solution container. To cover the antibody on the membrane evenly and to reach the result of combining with the antibody on the specific antigen, the overnight reaction and/or with the shaking way are commonly used in the conventional Western blotting method. However, this conventional method has some drawbacks, such as the high cost of the excessive antibody consumption and long operation time.

To reduce the antibody consumption, the drop injection or the spot coating has been used in the market. The biochemical molecules are coated on the carrier, such as the slice, membrane or chip etc., then the air dry or the oven dry is used. But the primary antibody cost and the operation time are still unable to meet the requirement of the fast reaction at user's end. Recently, a feasible approach is to take the advantage of microfluidic chip, such as the microchip electrophoresis etc., in which the antibody is driven by the voltage in the electrophoresis system, and then it is conjugated with target protein on the surface of porous membrane. Although this technology has the advantages of high sensitivity and high repeatability, but the high cost on chip fabrication has still limited its application.

In addition, by using high unit price of antibody to carry out the biochemistry and immunology test, it should always be considered to minimize the amount of antibody to reduce the cost under the required accuracy, and to offer multichannel detecting technology synchronously, in order to meet the goal of cost reduction, high-speed, abundance and accuracy.

In order to save the antibody consumption and reduce the operation time, the brand new thin-film direct coating method is designed and developed here. The film is coated on the substrate by the principle of the relative motion between the fluid and the substrate applied. The suitable coating interval, the fluid flow rate and the coating speed can be controlled to obtain the desired uniform thin wet film accurately. The thickness of the film determines the material consumption, and the diffusion distance among the molecules can be shortened to increase the reaction efficiency. However, when the thickness of liquid film is reduced to a critical thickness, the ratio of the surface area and the volume of the membrane will be increased. The liquid film tends to reduce the total surface area to reach the minimum surface energy, so that the film will break and shrink nonuniformly to cause the uneven concentration and fail the detection. This is the difficult point of the prior art which could be also prevented by the present invention. The purpose of the present invention is to effectively increase the detection efficiency and reduce the processing cost by the premise without sacrificing the signal-to-noise ratio and reliability. Up to now, there is no uniform coating method and the reaction technique of the biochemical molecules similar to the present invention.

SUMMARY OF THE INVENTION

The present invention provides a method for the uniform reaction on the porous materials, particularly to a method for enhancement of uniform reaction on porous materials. After the first reactant (such as target protein) is transferred onto the porous material (such as polyvinylidene difluoride, PVDF) which is subsequently placed on the platform of the machine, a small amount of second reactant (such as antibody) is injected into a compact coater. Then, all parameters are set on the machine. The coating head maintains a constant coating distance above the membrane and has no contact with the porous material (such as polyvinylidene difluoride). The reactant (such as antibody) is distributed and diffused uniformly on the porous material (such as polyvinylidene difluoride) by the coating head and the capillary force.

The present invention provides an example of corresponding antibody that was uniformly coated on the porous PVDF material blotted with another reactant (such as target antigen). The reaction collision probability is increased and the need of the reactant-dosage consumption is reduced by increasing the area-to-volume ratio at the reaction interface. The steps comprise the followings: providing a thin-film direct coating method and an adjustable coating width, uniformly coating a reactant (such as antibody) film on another reactant (such as target antigen).

The present invention provides an uniform chemical reaction to enhance for uniformly coating a reactant film on the porous materials, the steps comprise the followings: providing a thin-film coating method, a porous material, and a negative pressure vacuum apparatus. Wherein, the thin-film coating method comprises a coating head, which is for uniformly coating the reactant on a porous material. The porous material comprises a characteristic pore diameter. The suction direction of negative pressure vacuum apparatus is not parallel to the film coating direction. A forced convection is produced, that forces the reactant (such as antibody) moving in the direction to another reactant (such as target antigen), and then inhibit the reactant moving to other directions due to the diffusion mechanism and cause the local concentration of reactant being higher. When the interaction of reactant (such as antibody) and another reactant (such as target antigen) is increased, the signal-to-noise ratio can be increased.

The present invention provides a method for enhancement of the uniform reaction on the porous materials, which is a quick, miniaturized and uniform coating method to reach the cost reduction, high-speed, the mass production and the precision products for the market requirements.

The present invention provides a method for enhancement of the uniform reaction on the porous materials. Comparing with the conventional Western blotting method, the present invention needs much less processing time (at least one order of magnitude), and much less amount of the reagent dosage (at least two orders of magnitude) to reach the same detection signal strength.

The present invention provides a method for enhancement of the uniform reaction on the porous materials, which is a quick, miniacturized and uniform coating method, and can be widely applied in biochemistry and immunology etc. for the huge market requirements.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the following description, the attached Figures will be used to describe the implementation of the present invention. In the Figures, the same symbol of element is used to represent the same element. Also, in order to explain clearly, the size or thickness of the element may be exaggerated.

Figure 1:
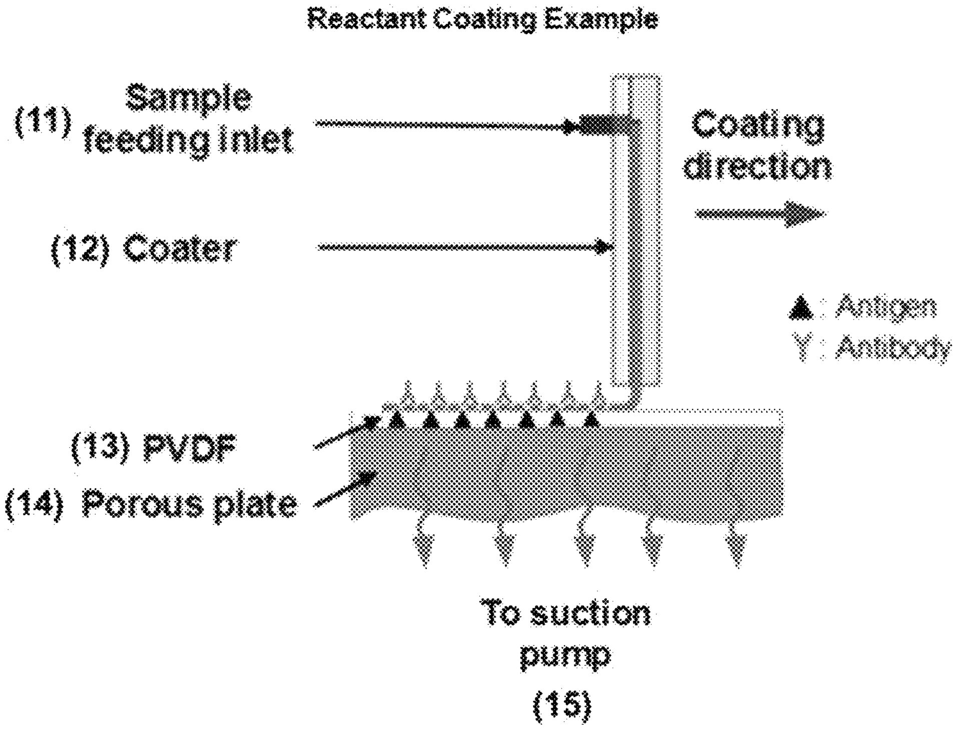
FIG. 1 illustrates an embodiment and method for enhancement of the uniform reaction on the porous materials in the present invention.

As shown in FIG. 1, an embodiment for a method for enhancement of the uniform reaction on the porous materials in the present invention is illustrated. After another reactant (such as target antigen) is transferred to the polyvinylidene difluoride membrane, which is subsequently placed on the platform of the machine. A small amount (at least two orders of magnitude less than the conventional Western blotting method) of reactant (such as antibody) is injected into through the coater inlet (11) into a light, compact and thin coater (12), then, all parameters could be set on the machine. The coating head (12) maintains a constant coating distance above the membrane and has no contact with the porous material. The reactant (such as antibody) is distributed and diffused uniformly on the porous material (such as polyvinylidene difluoride, PVDF) (13) from the coating head (14) by the surface tension.

Figure 2:
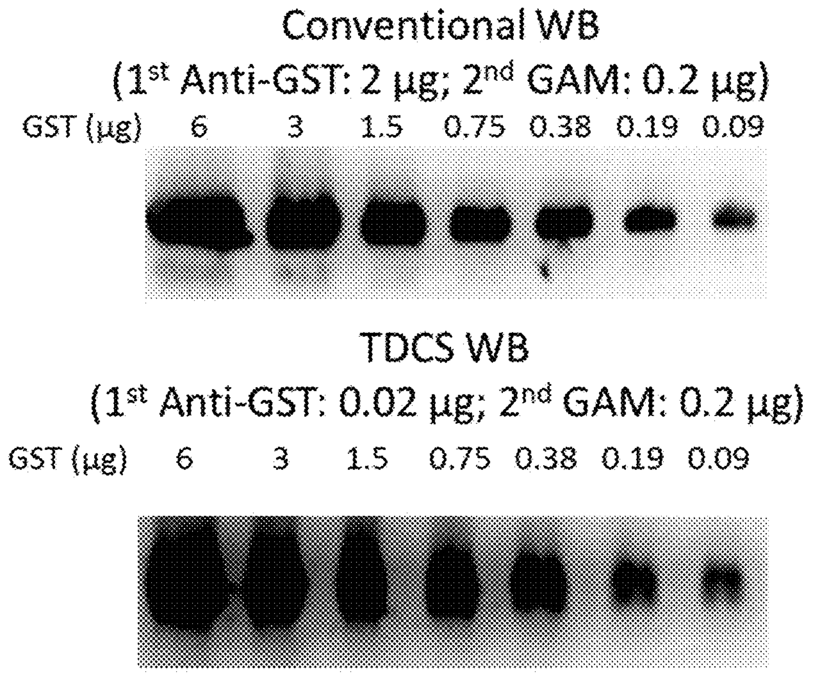
FIG. 2 illustrates the examples of experimental results for enhancement of the uniform reaction on the porous materials in the present invention.

As shown in FIG. 2, the experimental results for the enhancement method of a uniform reaction on the porous materials in the present invention are illustrated. Except that reactant (such as antibody) consumption of the present invention can be significantly reduced, it (such as antibody) can also contact the antigen (such as proteins or peptides) blotted membrane (such as polyvinylidene difluoride, PVDF) uniformly, so that the antibody can effectively combine with the particular antigen, and increase the sensitivity of conventional Western blotting method.

A method for enhancement of the uniform reaction on the porous materials is described in the present invention. Firstly, a thin-film direct coating method is used to distribute the reactant (such as antibody) on the membrane (such as polyvinylidene difluoride, PVDF) (13). The present invention collects the coating head, injection pump and/or surface tension as the fluid driving force. The reactant (such as antibody) is coated on the polyvinylidene difluoride membrane which has been blotted with another reactant (such as target antigen).

A method for enhancement of the uniform reaction on the porous materials is described in the present invention. In the coating process, the speed of coating membrane, distance and the flow rate of transport fluid are controlled. The abovementioned speed of coating membrane, distance and the flow rate of transport fluid should be precisely matched, so that the reactant (such as antibody) will form a uniform and very thin liquid film after the coating is finished, and the combination time for the reactant (such as antibody) probing with the another reactant (such as target antigen) by the diffusion mechanism, which can be shortened. Because the film thickness of per unit area is positive proportional to the reactant (such as antibody) amount of per unit area, that is, in the premise of the evenly liquid membrane, the reactant (such as antibody) on every place of liquid membrane will be distributed uniformly to obtain uniform dyeing color.

A method for enhancement of the uniform reaction on the porous materials is described in the present invention, in which the vacuum is used to prevent the uneven distribution for the diffusion of reactant (such as antibody). The reactant (such as antibody) contacting the membrane which has been blotted with another reactant (such as target antigen) by the thin-liquid film type is different with the diffusion phenomenon appeared when the antibody consumptions is getting much more as the prior art. At this moment, the ratio of the volume to the surface area for the membrane is increased, the liquid membrane trends to reduce the overall surface area, in order to reach the minimum low surface energy, it makes the membrane is easy to be broken by shrinking, to become as the liquid pearl, and leading to the uneven concentration.

A method for enhancement of the uniform reaction on the porous materials is described in the present invention, wherein the vacuum pump is used to force the convection of the reactant (such as antibody) by a negative pressure, the reaction time is further shortened and the noise signal caused by the non-specific combination is reduced. The present invention uses a vacuum pump to force the reactant (such as antibody) moving to another reactant (such as target antigen) by a negative pressure, and inhibit the reactant (such as antibody) moving to other directions due to diffusion mechanism and cause the local concentration of reactant (such as antibody) being higher. Upon interaction of the reactant (such as antibody) and another reactant (such as target antigen) is increased, the unreacted expensive antibody without combining with the target protein can be recovered and the signal-to-noise ratio can be increased. Through the automatic modularized, light, compact and thin coater as well as the vacuum pump, the machine is already verified that the method of the present invention can significantly reduce the antibody consumption and the operation time, reduce the human error, increase the detection efficiency, and sufficiently comply with the requirements of quick biomedical detection in the future.

The present invention for uniformly coating a reactant (such as antibody) film on another reactant (such as target antigen) by increasing the area-volume ratio of the reaction interface increases the reaction collision probability and reduces the whole reactant dosage. The method comprises the followings: providing a thin-film coating method and an adjustable coating width, and uniformly coating a reactant (such as antibody) film on another reactant (such as target antigen).

The present invention provides a uniform chemical reaction to enhance for uniformly coating a reactant film on the porous materials. The steps comprise the followings: providing a thin-film coating, a porous material, and a negative pressure vacuum apparatus. Wherein, the thin-film coating method comprises a coating head for uniformly coating the reactant on a porous material substrate. The porous material comprises a characteristic pore diameter for blotting with target reactant and washing with solution smoothly. The suction direction of negative pressure vacuum apparatus is not parallel to the flat direction of the thin-film coating. A forced convection is produced, that forces the reactant moving to the direction of another reactant (such as target antigen), and then inhibit the reactant moving to other directions due to the diffusion mechanism and cause the local concentration of reactant being higher. When the interaction of reactant (such as antibody) and another reactant (such as target antigen) is increased, the signal-to-noise ratio can be increased.

The present invention has the quick detection function, because the premise is for reducing the detection time established under the same developing effect. This method uses the fluid characteristics of the thin film, which shortens the diffusion distance between the reactant (such as antibody) and another reactant (such as target antigen), and uses a vacuum pump to force the antibody moving to the target protein by controlling a negative pressure, in order to inhibit the reactant moving to other directions due to diffusion mechanism and cause the local concentration of reactant being higher, and increase the interaction of the antibody and the target protein to reach the quick reaction.

The antibody consumption of the conventional immunoreaction, such as Western blotting method, should be at least greater than 2 μg. In the embodiment of the present invention, the thin-film direct coating method is adopted, only 0.02 μg or even less of antibody is required to coat on the polyvinylidene fluoride membrane, the content of target protein and the change of signal still can be detected stably and precisely. Upon carrying out the high-price biochemical detection, the primary antibody cost can be lowered under 1/100, which is significant advancement compared with the existing technique.

The present invention provides a method for enhancement of the uniform reaction on the porous materials, which is the quick, miniaturized and uniform coating method to reach the cost reduction, high-speed, the mass production and the precision products and the market requirements. The present invention provides a method for enhancement of the uniform reaction on the porous materials. Also, comparing with Western blotting method, the present invention needs only one order of magnitude less of the processing time, and two orders of magnitude less amount of the reactant dosage to reach the same detection signal strength. Summary by the abovementioned, the present invention provides a method for enhancement of the uniform reaction on the porous materials, which is quick, miniaturized and uniform coating method, and can be widely applied in biochemistry and immunology etc. for the huge market requirements.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed:

1. A method by using a machine to uniformly coat to form a thin-film on a porous material with a first reactant and enhance a chemical reaction between said first reactant and said second reactant of said thin-film by a negative pressure, comprising:

placing said porous material with said first reactant transferred on a platform of said machine:

preparing a coater having a coater inlet and a coating head of said machine with said second reactant by injecting said second reactant through said coater inlet into said coater, a coating distance being formed between said coating head and said porous material;

distributing uniformly said second reactant with a fluid flow rate from a coating head of said coater to coat said second reactant with a coating speed on said porous material to form said thin-film;

diffusing uniformly said second reactant of said thin-film on said porous material;

using said negative pressure in a direction of being non-parallel to a flat direction of said thin-film by forcing convention to force said second reactant of said thin-film moving to said first reactant combined on said porous material;

wherein, said porous material comprises a characteristic pore diameter for washing with a solution smoothly.

* * * * *